US010667895B2

(12) United States Patent
Alexander et al.

(10) Patent No.: US 10,667,895 B2
(45) Date of Patent: Jun. 2, 2020

(54) IMPLANTS, TOOLS, AND METHODS FOR TREATMENTS OF PELVIC CONDITIONS

(75) Inventors: James A. Alexander, Excelsio, MN (US); Scott S. Jeutter, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 402 days.

(21) Appl. No.: 14/128,991

(22) PCT Filed: Jun. 29, 2012

(86) PCT No.: PCT/US2012/044913
§ 371 (c)(1),
(2), (4) Date: Apr. 1, 2014

(87) PCT Pub. No.: WO2013/003714
PCT Pub. Date: Jan. 3, 2013

(65) Prior Publication Data
US 2014/0221733 A1    Aug. 7, 2014

Related U.S. Application Data

(60) Provisional application No. 61/503,009, filed on Jun. 30, 2011, provisional application No. 61/503,014, filed on Jun. 30, 2011.

(51) Int. Cl.
*A61F 2/00*     (2006.01)
*A61B 17/04*    (2006.01)
(Continued)

(52) U.S. Cl.
CPC ........ *A61F 2/0063* (2013.01); *A61B 17/0401* (2013.01); *A61B 17/064* (2013.01);
(Continued)

(58) Field of Classification Search
CPC ........ A61B 17/0493; A61B 2017/0495; A61B 2017/0429
(Continued)

(56) References Cited

U.S. PATENT DOCUMENTS

| 5,112,344 A | 5/1992 | Petros |
| 5,611,515 A | 3/1997 | Benderev et al. |

(Continued)

FOREIGN PATENT DOCUMENTS

| WO | WO2003/096929 | 11/2003 |
| WO | WO2007/016083 | 2/2007 |

(Continued)

*Primary Examiner* — Kaylee R Wilson
(74) *Attorney, Agent, or Firm* — Brake Hughes Bellermann LLP

(57) ABSTRACT

Described are various embodiments of surgical procedures, systems, implants, devices, tools, and methods, useful for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the implants that are useful for anchoring an implant to tissue.

19 Claims, 5 Drawing Sheets

(51) Int. Cl.
  *A61B 17/068* (2006.01)
  *A61B 17/064* (2006.01)
  *A61B 17/00* (2006.01)

(52) U.S. Cl.
  CPC .......... *A61B 17/068* (2013.01); *A61F 2/0045* (2013.01); *A61B 2017/00805* (2013.01); *A61B 2017/0414* (2013.01); *A61B 2017/0417* (2013.01); *A61B 2017/0443* (2013.01); *A61B 2017/0464* (2013.01); *A61B 2017/0649* (2013.01); *A61F 2002/0072* (2013.01)

(58) Field of Classification Search
  USPC ........................................................ 606/233
  See application file for complete search history.

(56) References Cited

U.S. PATENT DOCUMENTS

| | | | |
|---|---|---|---|
| 5,842,478 A | 12/1998 | Benderev et al. | |
| 5,860,425 A | 1/1999 | Benderev et al. | |
| 5,899,909 A | 5/1999 | Claren et al. | |
| 6,039,686 A | 3/2000 | Kovac | |
| 6,042,534 A * | 3/2000 | Gellman | A61F 2/0045 600/30 |
| 6,110,101 A | 8/2000 | Tihon et al. | |
| 7,070,556 B2 | 7/2006 | Anderson et al. | |
| 7,101,395 B2 | 9/2006 | Tremulis et al. | |
| 7,285,086 B2 * | 10/2007 | Smith | A61B 17/06066 600/30 |
| 7,351,197 B2 | 4/2008 | Montpetit et al. | |
| 7,422,557 B2 | 9/2008 | Arnal et al. | |
| 7,500,945 B2 | 3/2009 | Cox et al. | |
| 7,740,576 B2 | 6/2010 | Hodroff et al. | |
| 8,597,173 B2 | 12/2013 | O'Hern et al. | |
| 2002/0028980 A1 * | 3/2002 | Thierfelder | A61B 17/00234 600/37 |
| 2002/0082619 A1 * | 6/2002 | Cabak | A61B 17/0469 606/151 |
| 2002/0143234 A1 | 10/2002 | LoVuolo | |
| 2004/0006353 A1 * | 1/2004 | Bosley, Jr. | A61B 17/06109 606/151 |
| 2005/0216059 A1 * | 9/2005 | Bonutti | A61B 17/0487 606/232 |
| 2005/0288709 A1 * | 12/2005 | Fallin | A61B 17/0487 606/232 |
| 2006/0025649 A1 | 2/2006 | Smith et al. | |
| 2006/0195007 A1 | 8/2006 | Anderson et al. | |
| 2006/0195010 A1 | 8/2006 | Arnal et al. | |
| 2006/0195011 A1 | 8/2006 | Arnal et al. | |
| 2006/0265042 A1 | 11/2006 | Catanese, III et al. | |
| 2006/0287571 A1 | 12/2006 | Gozzi et al. | |
| 2008/0091058 A1 | 4/2008 | Bosley et al. | |
| 2009/0240104 A1 * | 9/2009 | Ogdahl | A61B 17/0401 600/37 |
| 2010/0125297 A1 * | 5/2010 | Guederian | A61B 17/0401 606/232 |
| 2010/0179575 A1 * | 7/2010 | Von Pechmann | A61B 17/0401 606/151 |
| 2010/0197999 A1 | 8/2010 | Deegan et al. | |
| 2010/0256442 A1 | 10/2010 | Ogdahl et al. | |
| 2010/0312051 A1 | 12/2010 | Brown | |
| 2011/0022061 A1 * | 1/2011 | Orphanos | A61B 17/0401 606/139 |
| 2011/0034759 A1 | 2/2011 | Ogdahl et al. | |
| 2011/0124956 A1 | 5/2011 | Mujwid et al. | |
| 2012/0290002 A1 * | 11/2012 | Astorino | A61B 17/0401 606/232 |

FOREIGN PATENT DOCUMENTS

| | | |
|---|---|---|
| WO | WO2007/097994 | 8/2007 |
| WO | WO2007/149348 | 12/2007 |
| WO | WO2009/075800 | 6/2009 |
| WO | WO2010/093421 | 8/2010 |

* cited by examiner

IMPLANTS, TOOLS, AND METHODS FOR TREATMENTS OF PELVIC CONDITIONS

CROSS REFERENCE TO RELATED APPLICATION

This application claims the benefit from International No. PCT/US2012/044913, which was granted an International filing date of Jun. 29, 2012, which in turns claims priority under 35 U.S.C. § 119(e) of U.S. Provisional Patent Application No. 61/503,009, filed Jun. 30, 2011, titled "Implants, Tools, and Methods for Treatments of Pelvic Conditions, and U.S. Provisional Patent Application No. 61/503,014, filed Jun. 30, 2011, titled "Implants, Tools, and Methods for Treatments of Pelvic Conditions," which applications are incorporated herein by reference in their entireties.

TECHNICAL FIELD

The present invention relates generally to implants, tools, devices, systems, apparatus, and related methods for treating pelvic conditions including but not limited to incontinence and prolapse conditions in men and women.

BACKGROUND

Pelvic health for men and women is a medical area of increasing importance, at least in part due to an aging population. Examples of common pelvic ailments include incontinence (e.g., urinary or fecal), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Urinary incontinence can be characterized by the loss or diminution in the ability to maintain the urethral sphincter closed as the bladder fills with urine. Male or female stress urinary incontinence (SUI) generally occurs when the patient is physically stressed.

Other pelvic floor disorders include cystocele, rectocele, enterocele, and prolapse such as anal, uterine and vaginal vault prolapse. Pelvic disorders such as these can result from weakness or damage to normal pelvic support systems.

In its severest forms, vaginal vault prolapse can result in the distension of the vaginal apex outside of the vagina, and is often associated with a rectocele, cystocele or enterocele. An enterocele is a vaginal hernia in which the peritoneal sac containing a portion of the small bowel extends into the rectovaginal space. Vaginal vault prolapse and enterocele represent challenging forms of pelvic disorders for surgeons. One known method of repairing vaginal vault prolapse is by suturing to the supraspinous ligament or attaching the vaginal vault through mesh or fascia to the sacrum. In particular, abdominal sacral colpopexy procedures are considered to be particularly effective treatments, however, such procedures can be relatively invasive and are somewhat complicated. An additional consideration is that many patients suffering from vaginal vault prolapse also require a surgical procedure to correct stress urinary incontinence that is either symptomatic or latent. In some cases, in order to correct one or more of these issues, the procedures that are often used involve lengthy surgical procedure times and/or lengthy recovery periods.

There is therefore desirable to provide a minimally invasive yet highly effective implantable system that can be used to treat incontinence, and/or pelvic organ prolapse and other conditions. It is further desirable that such a system can be delivered via minimally invasive (e.g., laparoscopic or transvaginal) surgical procedures, although improvements in systems and procedures that involve more invasive surgical procedures are also desirable.

SUMMARY

Various surgical tools, implants, and procedural improvements are disclosed herein. Certain embodiments of methods and implants involve tissue anchors and tensioning devices for attaching sutures, mesh, or other devices to the anatomy, such as for treating incontinence and/or prolapse. Embodiments of the anchors include a protective cap that can help to prevent damage to adjacent tissues.

An embodiment of the invention relates generally to fixation or attachment devices ("anchors") and related methods for placing a pelvic mesh implant, such as for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Embodiments of the implants can include a tissue support portion and one or more anchors, arms and the like. In addition, disclosed are devices and related methods useful for anterior or posterior prolapse repair with other treatments for pelvic floor disorders such as urinary incontinence, pelvic floor decent (levator avulsion), and/or sacral fixation. The implants can be adjustable after implantation, such as through an aperture at an end of one or more components. In order to provide a relatively even distribution of force and prevent or minimize coning or bunching of material, the implants can be provided with one or more load distribution elements.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
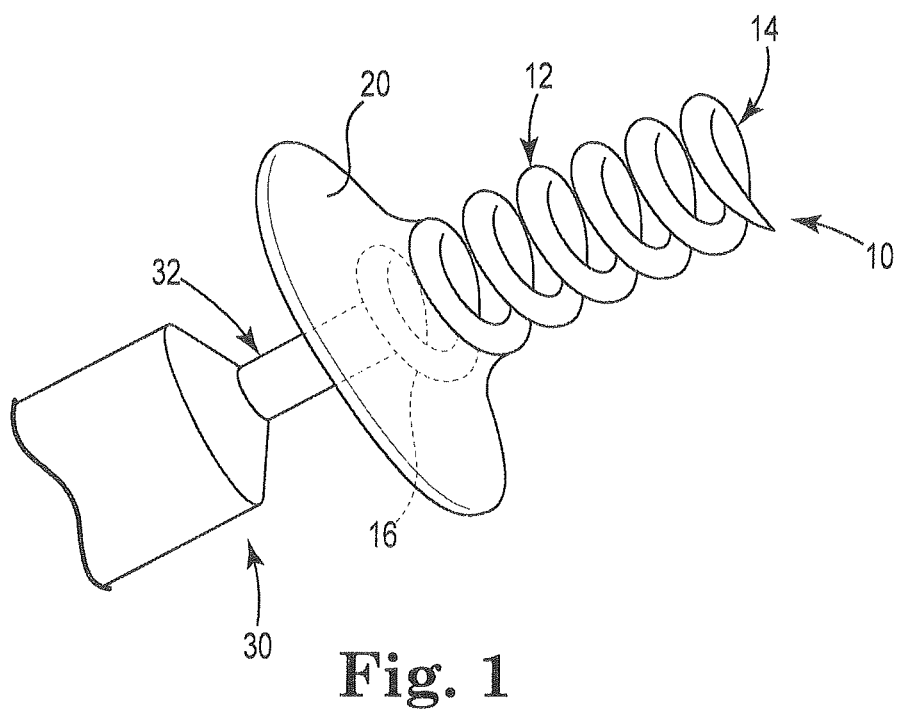
FIG. 1 is a perspective view of helical anchor of the invention as it can be positioned relative to a driver.

Pelvic floor disorders include cystocele, rectocele, enterocele, and uterine and vaginal vault prolapse, levator defects, among others, in male and female patients. These disorders typically result from weakness or damage to normal pelvic support systems. The most common etiologies include childbearing, removal of the uterus, connective tissue defects, prolonged heavy physical labor and postmenopausal atrophy.

Vaginal vault prolapse is the distension of the vaginal apex, in some cases to an orientation outside of the vagina. Vaginal vault prolapse is often associated with a rectocele, cystocele or enterocele. It is known to repair vaginal vault prolapse by suturing the vaginal vault (e.g., by stitches) to the supraspinous ligament or by attaching the vaginal vault through mesh or fascia to the sacrum. Many patients suffering from vaginal vault prolapse also require a concurrent or subsequent surgical procedure to correct stress urinary incontinence that is either symptomatic or latent.

In order to place a sling to stabilize or support the bladder neck or urethra, such as for the treatment of incontinence, surgical procedures and devices are often used. There are a variety of different sling procedures, where the slings used for pubovaginal procedures vary widely in the types of material and anchoring methods. In some cases, the sling is placed under the bladder neck and secured via suspension sutures to a point of attachment (e.g., bone) through an abdominal and/or vaginal incision. Examples of sling procedures are disclosed, for example, in U.S. Pat. Nos. 5,112,344; 5,611,515; 5,842,478; 5,860,425; 5,899,909; 6,039,686, 6,042,534 and 6,110,101.

A sacral colpopexy is one procedure used for providing vaginal vault suspension. It may be performed through an abdominal incision, a vaginal incision, or laparoscopically. A sacral colpopexy entails suspension (by use of an implant such as a strip of mesh) of the vaginal cuff to a region of sacral anatomy such as the sacrum (such as may be accomplished using bone screws that are implanted into the sacrum), a nearby sacrospinous ligament, uterosacral ligament, or anterior longitudinal ligament at the sacral promontory. An implant such as a synthetic mesh can be carefully customized or assembled into a special shape by the surgeon. In some sacral colpopexy procedures that also involve a hysterectomy, an implant can alternatively be attached to posterior vaginal tissue that remains after removal of the uterus and cervix, and also to anatomy to support the vaginal tissue at or around the sacrum, such as to uterosacral ligaments or to the sacrum itself (i.e., to a component of the sacral anatomy).

As used herein, the term "anchor" refers to any structure that can connect an implant to tissue of a pelvic region. The tissue may be bone, or a soft tissue such as a muscle, fascia, ligament, tendon, or the like. The anchor may be any known or future-developed structure, or a structure described herein, useful to connect an implant to such tissue, including but not limited to a clamp, a suture, a soft tissue anchor such as a self-fixating tip, a bone anchor, any of the structures described herein to be useful to connect an implant to soft tissue or bone of a pelvic region, or the like.

The systems and implants described herein are useful with surgical instruments, assemblies, implantable articles, systems and related methods for treating a pelvic condition including prolapse (e.g., any form of vaginal prolapse), urinary and fecal incontinence, levator defects, etc., in a male or female patient. An implant can be implanted in a male or a female to treat a condition such as urge incontinence, mixed incontinence, overflow incontinence, functional incontinence, and the like.

An implant can include a tissue support portion (or "support portion") that can be used to support a urethra or other pelvic tissue. Supporting a "urethra" refers to supporting tissue that includes the urethra (which can refer to the bladder neck) and that can optionally include tissue adjacent to a urethra such as bulbospongiosus muscle, corpus spongiosum, or both. According to specific methods involving treatment of urinary incontinence, a support portion may be placed below bulbospongiosus muscle to support both bulbospongiosus muscle and corpus spongiosum (along with the urethra), or alternately bulbospongiosus muscle may be dissected and a support portion may be placed to contact corpus spongiosum tissue (to support the urethra).

An implant can additionally include one or more extension portions attached or attachable to the tissue support portion. Normally, for treating incontinence, an implant can include two opposing extension portions. Extension portions are elongate pieces of material (e.g., mesh, suture, or biologic material) that extend from the tissue support portion and either are or can be connected to the tissue support portion, and are useful to attach to anatomical features or "supportive tissue" in the pelvic region (e.g., using a self-fixating tip or another form of tissue fastener) to thereby provide support for the tissue support portion and the supported tissue. Generally for treating incontinence, two extension portions can extend from the opposite ends of a tissue support portion as elongate "ends," "arms," or "extensions," and may attach to supportive tissue in the pelvic region by extending through a tissue path to an internal anchoring point (see, e.g., Applicant's copending U.S. Patent Publication No. US2010/256442, the entirety of which is incorporated herein by reference), or may extend to an external incision, such as through an obturator foramen and through an external incision at a groin or inner thigh (see, e.g., Applicant's copending U.S. Patent Publication Nos. US 2006/0287571 and US 2011/0034759, along with WO 2010/093421, the entireties of which are all incorporated hereby by reference).

In exemplary uses, each extension portion can extend from the location of attachment with the tissue support portion, through pelvic tissue, and optionally be attached to supportive tissue within the pelvic region. For certain procedures the supportive tissue can be tissue adjacent to the urethra such as pelvic fascia; tissue between the urethra and an obturator foramen such as pelvic fascia; or tissue of an obturator foramen such as obturator fascia, obturator internus muscle, obturator membrane, obturator externus muscle, etc. For alternate procedures an extension portion can be sized to extend from the tissue support portion, through an obturator foramen, around a pubic ramus bone, and threaded (subcutaneously) back to a medial location such as near a medial incision. Dimensions of extension portions can allow them to reach between a tissue support portion placed to support a pelvic tissue, such as tissue of a urethra, vagina, anal sphincter, levator, etc. (at an end of the extension portion connected to the tissue support portion), and a location at which the distal end of the extension portion attaches to supportive tissue at or about the pelvic region. A length of an extension portion may be fixed (i.e., the extension portion does not include any form of length-adjustment mechanism). Alternate embodiments of implants may include an adjusting engagement that allows a physician to alter the length of an extension portion before, during, and/or after implantation.

An implant may include portions, pieces, or sections that are synthetic or of biologic material (e.g., porcine, cadaveric, etc.). Extension portions may be a synthetic mesh, for example, such as a polypropylene mesh, a suture, a biodegradable suture, etc. The tissue support portion may be synthetic (e.g., a polypropylene mesh) or biologic. Examples of implant products that may be similar to those useful according to the present description, include those sold commercially by American Medical Systems, Inc., of Minnetonka Minn., under the trade names "Apogee", "Perigee", and "Elevate" for use in treating pelvic prolapse (including vaginal vault prolapse, cystocele, enterocele, etc.), and under the trade names "Sparc", "Bioarc", "Monarc", "MiniArc", "InVance", and "AdVance" for treating urinary incontinence.

An example of a particular type of pelvic implant is the type that includes supportive portions including or consisting of a tissue support portion and two opposing extension portions extending from the tissue support portion. An implant that has exactly two extension portions can be of the type useful for treating urinary incontinence. The term "supportive portions" refers to portions of an implant that function to support tissue after the implant has been implanted, and specifically includes extension portions and tissue support portions. An implant (e.g., sling) for placement against a corpus spongiosum for treatment of urinary incontinence in a male patient may optionally and preferably include a widened central support to provide increased contact and frictional engagement with the corpus spongiosum. See, for example, Assignee's copending U.S. Publication No. US 2006/0287571 and U.S. Pat. No. 7,422,557, the entireties of which are both incorporated herein by reference.

Dimensions of a tissue support portion can include any dimensions useful to support urethra tissue for treating incontinence, prolapse, or another pelvic condition. A tissue support portion for use in treating incontinence can be of a sufficient length to support and optionally partially surround a urethra or urethra-supporting tissue. A width of a tissue support portion may optionally and preferably be greater than a width of extension portions and can be sufficiently wide to increase contact area and frictional forces between a tissue support portion and a tissue in contact with the tissue support portion. A tissue support portion may be part of a support portion piece that includes the tissue support portion and optionally some amount of opposing extension portions extending from ends of the tissue support portion.

Dimensions of extension portions can allow them to reach between a tissue support portion placed to support a pelvic tissue, such as tissue of a urethra, vagina, anal sphincter, levator, etc. (at an end of the extension portion connected to the tissue support portion), and a location at which the distal end of the extension portion attaches to supportive tissue at or about the pelvic region. A length of an extension portion may be fixed (i.e., the extension portion does not include any form of length-adjustment mechanism). Alternate embodiments of implants may include an adjusting engagement that allows a physician to alter the length of an extension portion before, during, and/or after implantation.

Implants as described can include a tissue fastener at a distal end or a distal portion of an extension portion, which is the end or portion not attached to a tissue support portion. The term "distal" as used herein (unless noted otherwise) generally refers to a direction toward a patient and away from a surgeon installing a device. A tissue fastener at a distal end or portion of an extension portion can be any of various types, including: a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120; U.S. patent application Ser. Nos. 12/223,846 and 12/669,099; and WO 2009/075800, the entireties of which are all incorporated herein by reference). An implant may also have one or more extension portions that do not include a tissue fastener, such as may be used if the distal end is designed to be secured to tissue by other methods (e.g., suturing), or is intended to pass through an obturator foramen and a tissue path around a pubic ramus bone, in which case the extension portion may optionally include a connector, dilator, or dilating connector, which connects to an elongate tool that can be used to either push or pull the connector, dilator, or dilating connector through a tissue path (e.g., to a medial incision).

One type of a tissue fastener that can be used with devices and methods of the invention is an implant that includes a self-fixating tip. A "self-fixating tip" in general can be a structure (sometimes referred to as a soft tissue anchor) connected at a distal end of an extension portion (or extension portion piece) that can be implanted into soft tissue (e.g., muscle, fascia, ligament, etc.) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through a medial incision to reach the interior of the pelvic region, e.g., at a location of an obturator foramen. The insertion tool may engage the self-fixating tip at an internal channel of the self-fixating tip, at an external location such as at an external surface of the base, at a lateral extension, or otherwise as desired, optionally in a manner to allow the insertion tool to push the self-fixating tip through an incision in a patient and through and into supportive tissue.

Exemplary self-fixating tips can include one or more lateral extensions that allow the self-fixating tip to be inserted into soft tissue and to become effectively anchored in the tissue. A lateral extension may be moveable or fixed. The size of the self-fixating tip and optional lateral extensions can be useful to penetrate and become anchored into the tissue. Exemplary self-fixating tips are described in Assignee's copending international patent application PCT US2007/004015, the entirety of which is incorporated herein by reference. Other structures may also be useful.

A self-fixating tip can have structure that includes a base having a proximal base end and a distal base end. The proximal base end can be connected (directly or indirectly, such as by a connective suture) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage, optionally by means of a release mechanism that can be selectively engaged and released) a distal end of an insertion tool to allow the insertion tool to be used to place the self-fixating tip at a location within pelvic tissue of the patient. A self-fixating tip can be made out of any useful material, generally including materials that can be molded or formed to a desired structure and connected to or attached to a distal end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

According to various systems, one or more instruments, insertion tools, adjusting tools, or the like, may be incorporated or used with an implant or method. Examples of useful tools include those that generally include one or more (stationary or moveable) thin elongate, relatively rigid shafts or needles that extend from a handle. The shaft can be a single elongate shaft or multiple separate elongate shafts extending from the handle, or one or more primary shafts that extend from the handle and that contain multiple branch or "tine" shafts that separate at the end of the primary shaft. The handle is located at a proximal end of the device and attaches to one end (a proximal end) of a shaft. According to some embodiments, a distal end of one or more shafts can be adapted to engage a portion of an implant, such as a tissue fastener (e.g., a self-fixating tip), in a manner that allows the insertion tool to engage and push the tissue fastener through a tissue passage and connect the tissue fastener to supportive tissue of the pelvic region. Examples of this type of tool can be used with a self-fixating tip that includes an internal channel designed to be engaged by a distal end of an insertion tool to allow the self-fixating tip to be pushed into tissue. Other general types of insertion tools will also be useful, but may engage a self-fixating tip or other tissue fastener in an alternate manner, e.g., that does not involve an internal channel.

Exemplary insertion tools for treatment of incontinence and vaginal prolapse are described, e.g., in U.S. patent application Ser. Nos. 10/834,943, 10/306,179; 11/347,553; 11/398,368; 10/840,646; PCT Application Nos. 2006/028828 and 2006/0260618; WO 2010/093421; and U.S. Patent Publication No. US 2010/0256442, the entireties of which are all incorporated herein by reference.

A tool that can be used for embodiments of the invention can optionally include a mechanism by which a tissue fastener (e.g., a self-fixating tip) can be securely and releasable engaged with a distal end of an insertion tool such that the tissue fastener can be selectively secured to the distal end mechanically, then selectively released. With a releasable engagement, a tissue fastener (e.g., self-fixating tip) can be released from the distal end by releasing the engagement (e.g., mechanical engagement) by movement of an actuator at the proximal end of the insertion tool, such as at the handle. For example, an internal channel (or external surface) of a self-fixating tip can include an engaging surface designed to engage a mechanism at a distal end of an insertion tool while the self-fixating tip is placed at, on, or over the distal end. As an example, an internal or external surface of a self-fixating tip can include a depression, ring, edge, or ledge, that can be rounded, angular, etc. A mechanical detent such as a pin, ball, spring, deflector, or other surface or extension located at the distal end of the insertion tool can be moved, deflected, or extended relative to the distal end of the insertion tool to contact the surface of the self-fixating tip to securely and releasably hold the self-fixating tip at the distal end of the insertion tool and prevent removal of the tip from the distal end until removal is desired. The detent (or other surface or mechanism) can be cause to extend (or retract) from the distal end of the insertion tool by actuating a trigger or other mechanism located at the proximal end (e.g., handle or a proximal location of a shaft) of the insertion tool, to secure (or release) the self-fixating tip. Upon placement of the self-fixating tip at a desired location during a surgical implantation procedure, the insertion tool operator can release the self-fixating tip by use of the trigger or other mechanism at the handle to disengage the detent and cause the tip to become loose. The insertion tool can then be removed from the tissue path, and the self-fixating tip can remain in a desired implanted location.

Optionally, an implant can include a tissue fastener at a location of a tissue support portion, or at a location along a length of an extension portion. This form of tissue fastener can be in the form of reinforced (e.g., by coating, heat treating, or a reinforcing weave or strip) edge extensions, multiple layers of mesh and edge extensions in an extension portion, etc., as described, for example, at Applicant's copending U.S. Pat. No. 7,422,557, and Applicant's copending United States Patent Publication Numbers US 2006/0195011, US 2006/0195007, and US 2006/0195010, all of which are incorporated herein by reference. Other examples include relatively rigid structures such as metal, plastic, or other polymeric or non-polymeric structure that may be shaped to frictionally engage soft tissue, for example to include a tine, hook, chevron, barb, arrow, etc., combinations thereof, or any structure added to an edge or surface of an extension portion to improve fixation within tissue. The structure can have any shape or form that will increase frictional force between the implant and adjacent tissue, such as one or multiple pointed surface directed along a length of an extension portion, toward the tissue support portion, and extending away from a surface or edge of the implant (e.g., extension portion). The tissue fastener can be located at a position of an implant that will result in the tissue fastener being located at supportive tissue such as muscle or fascia when the implant is placed with a midline of the tissue support portion being located below a urethra. For example, a tissue fastener may be located on a tissue support portion or an extension portion of an implant, e.g., as close as 2 or 3 centimeters from a midline of a tissue support portion, and up to a distance that reaches tissue of an obturator foramen when the midline is located below a urethra, e.g., up to 7 centimeter from the midline.

An implant can include multiple pieces that are adjustably connected together by an adjusting engagement. One example of a multiple piece implant is an implant that includes a "support portion piece" and one or multiple "extension portion pieces" as separate pieces of the implant. An extension portion piece can be separate from a support portion piece, and the two pieces can be connected through an adjustable engagement. The support portion piece can include a tissue support portion.

One form of implant useful for treatment of urinary incontinence is a "mini-sling," or "single incision sling," (e.g., as marketed by American Medical Systems under the trade name "MINIARC") have entered the market as a faster more minimally invasive procedure for treating female stress urinary incontinence. The adjustability on currently released traditional slings (such as retropubic and transobturator) is minimal. Adjustability of a sling allows for a broader use among physicians for a more diverse patient population. Designs described herein are also useful for female pelvic floor repair products, male incontinence, for treating prolapse (e.g., vaginal prolapse), levator defects, anal incontinence, and other pelvic conditions.

Figure 2:
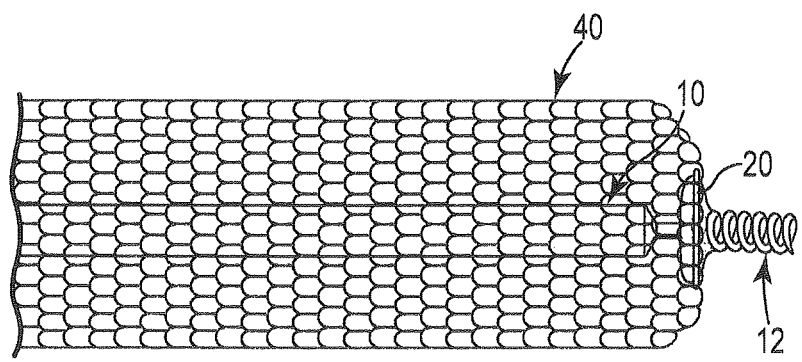
FIG. 2 is a side view of a helical anchor and driver of the type illustrated in FIG. 1, in combination with a mesh material.
Figure 3:
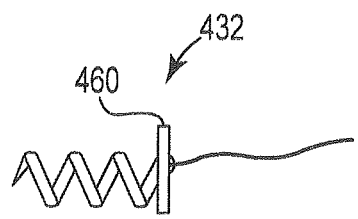
FIGS. 3-7 illustrate various anchor and delivery devices for use in piercing tissue and that can be used with a helical anchor of the type illustrated in FIGS. 1 and 2.
Figure 4:
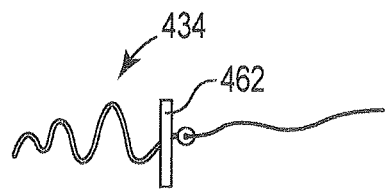
Figure 5:
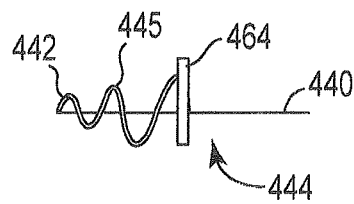

Referring now to the Figures, where like structure may be described with like reference numbers and/or terms, and initially to FIGS. 1 and 2, an embodiment of an anchor for use with an implantable system of the type described herein is illustrated, which can be used for vaginal vault suspension and attachment to the sacral promontory, as one example, although it may also be used for other procedures. The anchor can be used for attaching sutures, mesh, or other devices to treat incontinence, prolapse, and/or other pelvic disorders.

FIG. 1 illustrates an exemplary embodiment of a helical anchor 10, which may also be referred to as a coil tissue fixation element. Anchor 10 includes a coil portion 12 having a distal end 14 and a proximal end 16. Coil portion 12 may have threads with a generally constant pitch, or may instead have variable pitch threads for connection with the tissue to which it will be attached. Anchor 10 further includes a protective cap member 20, which is shown as being adjacent to the proximal end 16 of the coil portion and spaced from the distal end 14. However, the cap member 20 may instead be spaced further from the proximal end 16 than is illustrated in this figure, such as being positioned closer to the distal end 14 (e.g., in a more central location relative to the length of the coil portion 12), or being positioned further from the distal end 14, for example.

Cap member 20 may be a molded plastic element (e.g., polypropylene), for example, which can be molded directly onto the coil portion 12. However, the cap member 20 may instead be made of another material, such as metal, or a combination of materials. Rather than being directly molded onto the coil portion 12, the cap member 20 can instead be attached in another way, such as by threading the cap member 20 over the coil portion 12 or by slipping it over the outer diameter of the coil portion 12 and then securing it in its desired location along the length of the coil portion 12. Cap member 20 may be a generally circular disc, or may instead have a different shape, such as oval, elliptical, rectangular, or the like. Cap member 20 may have generally flat or planar surfaces on one or both sides, or one or both of its opposite surfaces can include at least a portion that is concave or convex. In any case, the cap member 20 can be designed and/or selected to provide a desired level of protection for the tissues that will be adjacent to the cap member when the anchor is implanted in a patient.

In an alternative embodiment, all or most of the helical anchor 10 may be a component that is completely injection molded, and therefore may comprise a single-piece or integral construction. That is, the coil portion 12 and cap member 20 can be molded together as one unit. In yet another alternative embodiment, the helical anchor may include barbs to prevent or minimize the possibility of the anchor "backing out" or unscrewing from the implantation site. Such barbs can be provided at any point along the coil portion 12, for example.

The cap member 20 may further include a keyway or other access feature on its proximal surface that is configured for engagement with a driver, such as the distal end of a driver 30 that is shown in FIG. 1 as being engaged with the helical anchor 10. The driver 30 is a tool that can be used to implant the anchor 10, and may have a wide variety of configurations. Embodiments of drivers or insertion tools that can be used for implantation of anchors, such as can be used for methods for treating pelvic conditions (e.g., a method of performing a transvaginal sacral colpopexy), can include a proximal end having a handle and an actuator, trigger, and/or other features. In one embodiment of the driver 30, the proximal end of the tool (e.g., a handle) extends from a proximal end of a shaft 32. The length and structure of the shaft in one embodiment is sufficient to allow a user to grasp and manipulate the proximal end (e.g., at the handle) as the shaft is extended through a vaginal incision (i.e., transvaginally) to place a distal shaft end generally at a location of a posterior pelvic region, (e.g., to place the distal shaft end at a location for placing an anchor at a component of sacral anatomy, such as an anterior longitudinal ligament at a sacral promontory). In another embodiment, the length and structure of the shaft is sufficient for a user to grasp and manipulate the proximal end of a device to move the distal shaft end through a laparoscopic incision (e.g., an abdominal incision) to place the distal shaft end at a desired location in the patient's anatomy.

The shaft 32 can include a longitudinal axis, and a distal end or tip (not visible in the figure). The tip is capable of engaging and holding (for manipulation) helical anchor 10 for insertion through a vaginal incision to a location of a posterior pelvic region where the helical anchor 10 can be fastened to tissue. In one embodiment, the cap member 20 is capable of being engaged with the tip of the driver, which the distal end of the coil portion 12 is capable of being placed in contact with tissue. When the cap member 20 is engaged with the tip of the driver 30 and the distal end of the anchor 10 is in contact with tissue or other structure, driver 30 can be rotated along its longitudinal axis. This rotation will cause a corresponding rotation of the helical anchor 10 relative to its longitudinal axis in a manner that allows the anchor to be rotationally advanced (e.g., driven) into the tissue or other structure.

FIG. 2 illustrates the helical anchor with a cap member 20 as it can be engaged with a distal end of a portion of an exemplary implant 40, such as an implant of the types described herein relative to various treatments of pelvic conditions. In one exemplary embodiment, the implant 40 is made at least partially of a mesh material that inherently includes multiple holes throughout the mesh. Rather than a mesh material, the implant 40 can be made of other materials. As shown with a mesh material in FIG. 2, the distal end 14 of the coil portion 12 can be inserted through a desired opening or aperture that extends through the implant 40. Alternatively, the distal end 14 of the coil portion 12 can be used to create a new opening in the implant 40 in such a way that its distal end 14 extends beyond the material. When engaged with an implant 40, the cap member 20 may be located on either side of the mesh material 40.

The driver 30 or other delivery tool can then be used to place the anchor 10 and mesh material 40 in proximity to their desired location in the patient. The helical anchor 10 is then engaged with tissue or other structure by rotating the driver until the anchor is securely implanted in the desired structure.

FIGS. 3-7 illustrate other exemplary anchor and delivery devices that can be used with a cap member of the type described above relative to its use with a helical anchor. The illustrated anchor and delivery devices are described and illustrated in U.S. Pat. No. 7,101,395, the entirety of which is incorporated herein by reference. In particular, a cap member 460 can be incorporated into the anchor assembly 432 of FIG. 3, which assembly includes a self-tapping thread or helix of sharpened wire. A cap member 462 can also be incorporated into the anchor assembly 434 of FIG. 4, which assembly includes a helix having a variable radii, such that the initial distal engaging coils of the helix are relatively small in diameter as compared to the diameter of the helix at its proximal end. A cap member 464 can also be incorporated into the anchor assembly 444 of FIG. 5, which assembly includes a coil 445 having a distal end 442 and a suture 440 extending from the distal end 442. In this embodiment, as more force is applied to the anchor by the suture, the coil 445 can tend to collapse upon itself to provide additional support to the tissue or other structure to which it is attached. With all of these embodiments, the cap member can be positioned further proximally or distally than shown in the figure, wherein the cap member can also be configured to have a different size or shape, as is discussed above relative to the cap member of FIGS. 1 and 2.

Figure 6:
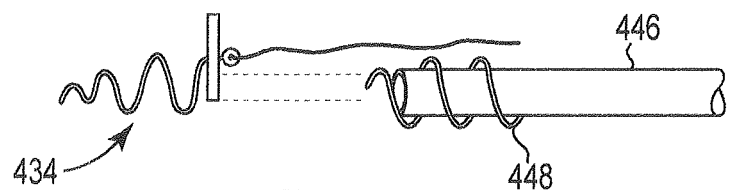

FIG. 6 illustrates delivery of an anchor 434, which can have a cap member in accordance with the invention incorporated along its length. The anchor 434 is secured to a releasable delivery shaft 446. In one method of delivery, the anchor 434 is secured to a target location using a rotational motion (e.g., clockwise). Engaging threads 448 on the delivery shaft 446 allows for this rotation of the anchor 434 during engagement with the target location. Rotation of the delivery shaft in the opposite direction (e.g., counterclockwise) will disengage the anchor 434 from the threads 448 on the delivery shaft, after which the delivery shaft can be removed from a guide catheter. The anchor 434 will then be secured within the target tissue.

Figure 7:
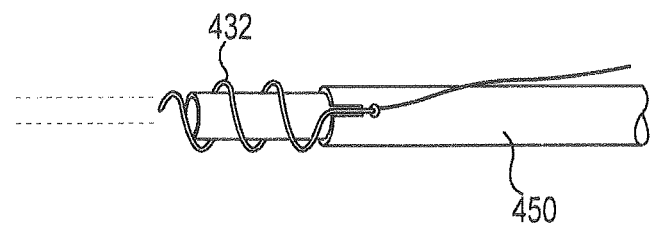

FIG. 7 illustrates a distal end of a guide catheter 450 as releasably locking or engaging at least a portion of the anchor 432, which can have a cap member incorporated along its length, in accordance with the invention. The anchor 432 is delivered with the engaging portion of the guide catheter 450 retracted. After delivery of the anchor 432, the guide can be advanced up to the anchor point to engage a portion of the anchor. Rotation of the delivery shaft 450 causes the anchor to be held in place while the delivery shaft disengages. The guide catheter 450 is then retracted from the anchor, thereby leaving the anchor secured to tissue.

Figure 8:
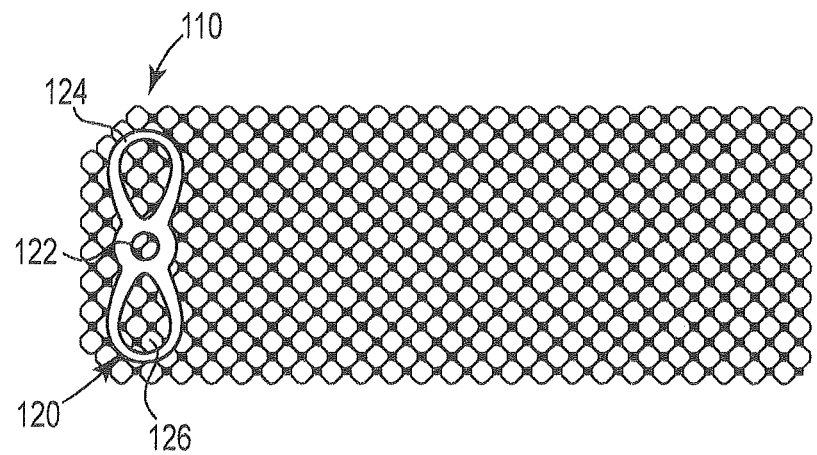
FIG. 8 is a top view of a portion of an embodiment of a mesh implant in accordance with the invention.
Figure 9:
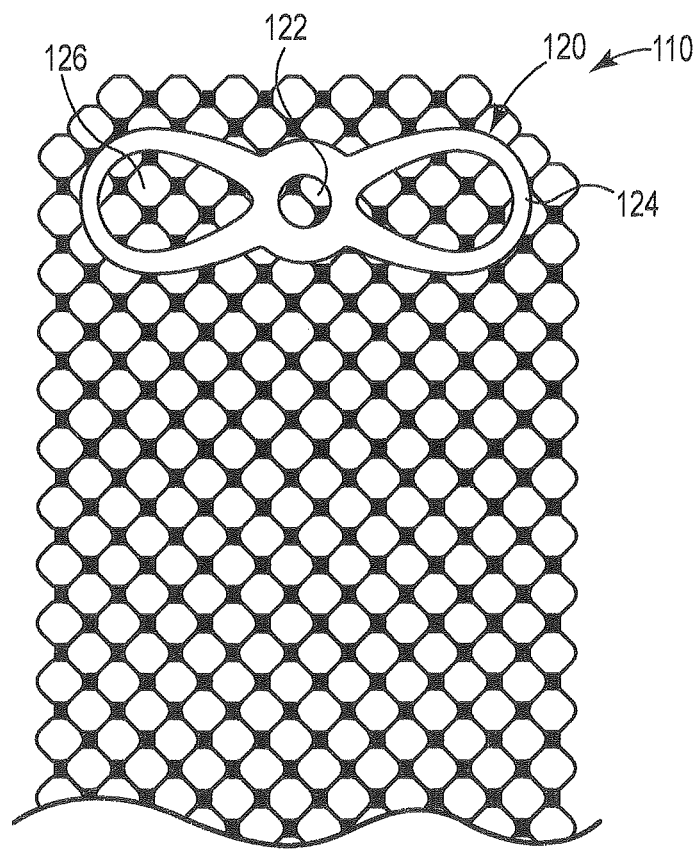
FIG. 9 is an enlarged top view of a portion of the mesh implant illustrated in FIG. 8.
Figure 10:
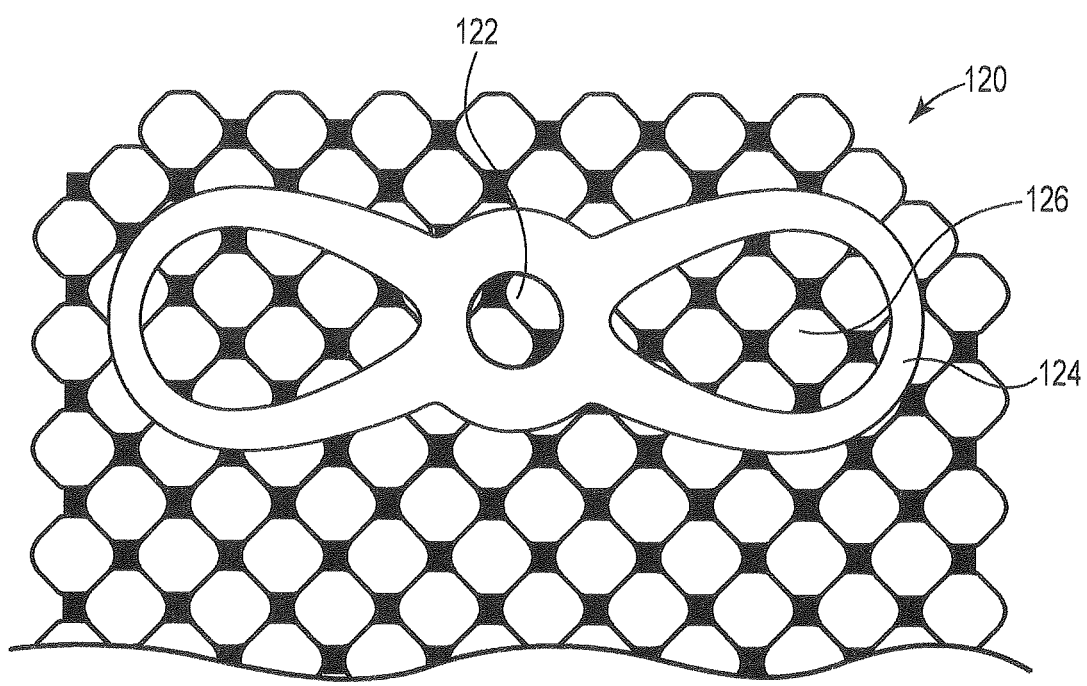
FIG. 10 is a further enlarged top view of a portion of the mesh implant illustrated in FIGS. 8 and 9.
Figure 12:
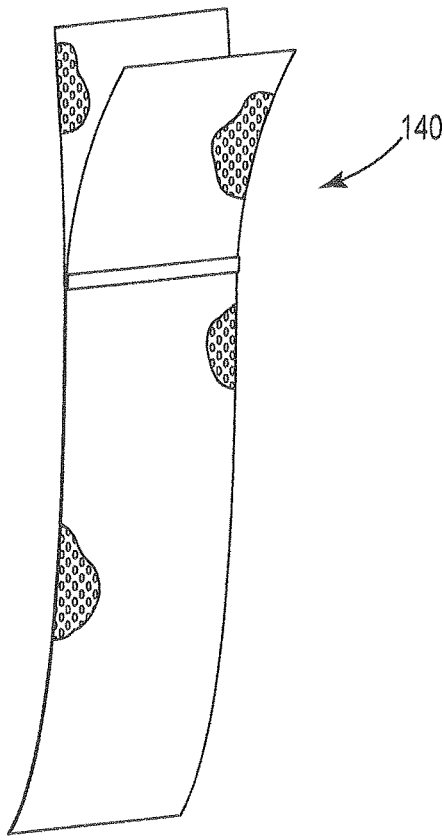
FIG. 12 is a perspective view of a mesh implant that is usable with embodiments of the invention.

Referring now to FIGS. 8-10, wherein like structure may be described with like reference numbers and/or terms, a portion of an embodiment of an implantable system is illustrated, such as can be used for vaginal vault suspension and attachment to the sacral promontory, for example. In particular, an end portion 110 of an implant (e.g., a mesh implant) is illustrated in the Figures, which includes a load distribution element 120 positioned generally adjacent to an end of the implant. The illustrated implant can be part of a Y-shaped mesh component that is designed to be attached to the sacral promontory at a first end, such as the exemplary implant 140 illustrated in FIG. 12. Such a Y-shaped mesh component 140 can include two elongated mesh portions that are arranged in a V-shape to provide an intersection or apex area. Alternatively, one or more of these elongated mesh portions can instead be an elongated polymeric portion. An extending base portion can from the apex area where the two elongated mesh portions meet to create the Y-shape of the implant 140. Any of the elongated mesh portions can be generally flat rectangular members that taper at one end, however, it is understood that the elongated mesh portions can instead have a different configuration. In accordance with the invention, load distribution element(s) can be incorporated into the structures of any of these elongated mesh portions.

In one embodiment of the invention, the end portion 110 of a mesh implant includes at least one eyelet or opening 122 that can be used for attachment of this portion to the sacral promontory or other anatomical structure. The eyelet or opening 122 is shown as positioned generally in a central area of the load distribution element 120. Element 120 further includes two extending members 124 extending outwardly from opposite sides of the eyelet 122. Extending members 124 are provided to distribute the stresses or loads that are placed on the eyelet 122 during and after a surgical implantation procedure. Such a load distribution can be beneficial to avoid a "coning" of material that makes up the implant and the anatomical structure to which it is attached that can sometimes occur when the load is concentrated in a small area. In other words, the end portion 110 of the mesh implant may tend to stay more flat when the load is more distributed than when the load is more concentrated. In a sacral colpopexy procedure, for example, the use of such a load distribution element can create an apical support that is flat or has a duckbill shape that more closely matches the shape that is created in other sacral colpopexy procedures.

Each of the extending members 124 may be configured as shown to include an outer frame area that surrounds an inner opening 126, although it is understood that the shape and specific configuration of these extending members 124 can vary from the illustration. For example, each of the inner openings 126 is shown to have a teardrop type of shape; however, the openings 126 can instead be more circular, oval, elliptical, rectangular, or any other desired shape. It is further understood that an embodiment of the load distribution element 120 may include extending members 124 that solid across their lengths and widths, and that therefore do not include an inner opening 126. The outer frame area of the extending members 124 may also include a variety of shapes that differ from those in the illustrations. For example, the outer shape may be more rounded, oval, irregular, or any other desired shape, although a preferred embodiment will include an outer shape that does not have any sharp or protruding features that can interfere with the area surrounding the implant either during or after its implantation in a patient.

With further reference to the extending members 124, although two similarly sized and shaped extending members 124 are illustrated in the Figures, it is understood that the load distribution element 120 may instead include more or less than two extending members and/or that multiple extending members of a single load distribution element may have different sizes and/or shapes from each other. In addition, although the figures illustrate the inner openings 126 as having an outer shape that generally matches the outer shape of the outer frame area, which thereby makes the width of the outer frame area generally consistent around its edges, the inner openings 126 can instead have an outer shape that is somewhat or substantially different than the outer shape of the outer frame area. It is also understood that a single implant may include more than one of these load distribution elements at the same end of an implant, such as can be used if more than one eyelet is desirable for securing the implant within the patient.

The implants with which the load distribution elements described above can be used can be made of a number of different materials. For example, the various mesh members and portions can be constructed of polymeric materials, such as a thin film or sheet material of polypropylene, polyethylene, fluoropolymers or like compatible materials, both permanent and absorbable. The mesh can be laser cut from a sheet, or may consist of filaments and fibers that are arranged relative to each other to provide a desired mesh material. Each load distribution element 120 may be made of the same material or a different material than the material from which the mesh is made. In one embodiment, the mesh is made of a polymeric material and the associated load distribution element is formed of the same material by pressing that polymeric material in its molten state onto the mesh. In another embodiment, the load distribution element is formed by melting or shaping the mesh of the implant itself (i.e., no additional material is added to the mesh to create the load distribution element). In yet another embodiment, a load distribution element is attached to the implant by adhesive or another attachment mechanism or material.

The eyelets of the implants described herein (e.g., eyelet 122) can be a one-way locking eyelet such that when a rod or other tool is pushed through the eyelet in an insertion direction, it is prevented from being pulled back out of the eyelet (i.e., in a direction that is opposite from the insertion direction). A tool such as a tensioning device can optionally be used to push the eyelet along the length of the elongated mesh portion and/or the base portion until a specific tension has been reached. A tool that includes a tension indicator gauge to measure tension can also be used, if desired.

Figure 11:
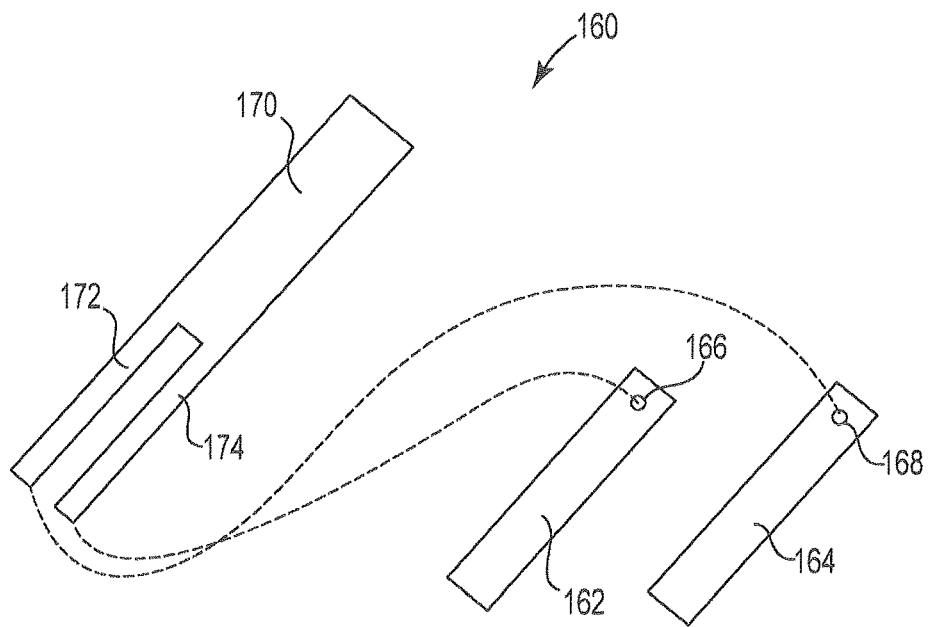
FIG. 11 is a top view of an adjustable vaginal support system.

The mesh implants of the invention can provide for an adjustability mechanism via an aperture through a mesh component that is designed to allow for elevation of the vaginal apex toward the sacrum in order to alleviate the symptoms of vaginal prolapse. Such systems can therefore be provided with adjustability at the vaginal walls and at the sacrum or sacral promontory, and can be used with either transvaginal, laparoscopic, or other surgical methods of supporting the apex of a vagina by fixation and support from a region of the sacral anatomy. One example of such an adjustable vaginal support system 160 is illustrated in FIG. 11, which provides for separate tensioning to the anterior and posterior compartments. This system can be used for sacral colpopexy or related procedures for supporting a vaginal apex, which can be performed using an anterior implant and a posterior implant.

With additional reference to FIG. 11, an anterior implant 162 and a posterior implant 164 are illustrated, each of which includes an aperture or eyelet 166, 168, respectively, located adjacent to one of its ends. Each of these implants 162, 164 can include an extending portion that extends beyond the area of the aperture in eyelet, wherein this extending portion allows for extra anterior or posterior support. The vaginal apex support system 160 further includes an additional member 170 that is provided for fixation to the sacrum. This adjustable implant system 160 therefore includes an adjustable vaginal apex support device with an anterior mesh piece 162, a posterior mesh piece 164, and an auxiliary piece 170 that is designed for fixation to the sacrum. These pieces are used in a system that allows for separate adjustment in vivo to obtain proper support of a vaginal apex. The anterior and posterior pieces 162, 164 are secured to an anterior and a posterior vaginal wall, respectively. The auxiliary piece 170 is secured to a region of sacral anatomy (e.g., an anterior longitudinal ligament or the sacrum). Tabs 172, 174 of the auxiliary implant 170 are inserted through eyelets 166, 168 on the anterior and posterior pieces 162, 164, respectively. Each tab 172, 174 can be adjusted through its corresponding eyelet, and tensioned separately at the vaginal apex with the auxiliary piece 170 being secured to the sacral anatomy. By selective movement of the tabs through the eyelets or openings, tension of the combined mesh implant and positioning and support of the vaginal apex can be adjusted.

Any or all of the eyelets of the mesh structures may be associated with a load distribution element of the type illustrated in FIGS. 8-10. In addition, any of the features of the mesh structures disclosed relative to FIGS. 8-12 may be used in combination with the helical anchors and cap members disclosed relative to FIGS. 1-7 in order to provide systems in which an anchor can be used to implant a mesh structure that has an improved load distribution at its attachment point as compared to a mesh structure that does not have such a load distribution feature.

The features described herein can be used with implants that provide support for pelvic tissue, and/or can be useful in conjunction with other methods of treating pelvic conditions, such as treating a levator hiatus, anal incontinence, etc. The disclosed implants, along with their various components, structures, features, materials and methods, may have a number of suitable configurations as shown and described in the previously-incorporated references. Various methods and tools for introducing, deploying, anchoring and manipulate device, implants, and the like as disclosed in the references incorporated herein are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. An implant for treating a pelvic condition, the implant comprising:
   a support portion;
   an elongated member including a proximal end connected to the support portion, a distal end, a length extending between the proximal end and the distal end, and a width; and
   a load distribution element adjacent to the distal end of the elongated member, the load distribution element including an outer frame member having a central aperture, a first elongate extending member extending from the central aperture in a direction of the width of the elongated member, a second elongate extending member extending from the central aperture in a direction of the width of the elongated member, the first elongate extending member including a first section and a second section, the first section being adjacent to the central aperture, the first section having a width smaller than a width of the second section, and wherein the first elongate extending member and the second elongate extending member are adapted to maintain a flat configuration across substantially an entire width of the elongated member by distributing a load placed on the central aperture along the width of the elongated member,
   the first elongate extending member defining a first opening, the first opening having a length and a width, the length being longer than the width, the length of the first opening extending along in the direction of the width of the elongated member.

2. The implant according to claim 1, wherein the first elongate extending member comprises generally planar top and bottom surfaces that are generally parallel to a top and bottom surface of the elongated member.

3. The implant according to claim 1, wherein the central aperture is located at a central area of the load distribution element.

4. The implant according to claim 1, wherein the first elongate extending member extends in the width direction relative to one side of the central aperture and the second elongate extending member extends in the width direction relative to an opposite side of the central aperture.

5. The implant according to claim 1, wherein the load distribution element comprises a molded piece attached to one of a top and bottom surface of the elongated member.

6. The implant according to claim 1, wherein the load distribution element is integrally molded with the elongated member.

7. The implant according to claim 1, wherein the elongated member comprises a mesh material.

8. The implant according to claim 1, wherein the implant is configured to treat a pelvic condition selected from the group consisting of: fecal incontinence, urinary incontinence, vaginal prolapse, anal prolapse, uterine prolapse, perineal descent, a levator defect, and rectal prolapse.

9. The implant according to claim 1, wherein the elongated member comprises mesh and wherein a portion of the mesh is located between the load distribution element and the elongated member distal end.

10. The implant according to claim 1, wherein the load distribution element is a first load distribution element, the implant further comprising:
a second load distribution element adjacent the first load distribution element.

11. The implant according to claim 1, wherein the load distribution element is a first load distribution element, and the elongated member is a first elongated member, the implant further comprising:
a second elongated member including a proximal end connected to the support portion, a distal end, a length extending between the proximal end and the distal end, and a width;
a second load distribution element adjacent to the distal end of the second elongated member, wherein the second load distribution element includes a central aperture and at least one extending member extending from the central aperture in the width direction.

12. The implant according to claim 11, wherein a distal end of the support portion is connected to the proximal end of the elongated member and the proximal end of the second elongated member to form a Y-shaped implant.

13. The implant of claim 11, wherein the second load distribution element has a width and a length, the width being greater than the length.

14. The implant of claim 1, wherein the load distribution element has a width and length, the width being greater than the length.

15. The implant of claim 1, wherein the central aperture, the first elongate extending member and the second elongate extending member are co-planar.

16. The implant of claim 1, wherein the central aperture, the first elongate extending member, and the second elongate extending member having a shape that generally matches an outer shape of the outer frame member.

17. The implant of claim 1, wherein the second elongate extending member includes a first section and a second section, the first section having a width smaller than a width of the second section.

18. The implant of claim 1, wherein the second elongate extending member defining a second opening, the second opening having a length and a width, the length being longer than the width, the length of the second opening extending along in the direction of the width of the elongated member, the first opening and the second opening being larger than the central aperture.

19. The implant according to claim 18, wherein the second opening has a shape different from the shape of the central aperture.

* * * * *